United States Patent [19]

Grunwald

[11] Patent Number: 4,492,229
[45] Date of Patent: Jan. 8, 1985

[54] SUTURE GUIDE HOLDER

[76] Inventor: Ronald P. Grunwald, 203 Deaconess Doctors Bldg., Spokane, Wash. 99204

[21] Appl. No.: 414,603

[22] Filed: Sep. 3, 1982

[51] Int. Cl.³ .............................................. A61B 17/00
[52] U.S. Cl. ............................. 128/303 R; 128/334 R
[58] Field of Search ......................... 128/303 R, 334 R

[56] References Cited

U.S. PATENT DOCUMENTS

| 784,018 | 2/1905 | Witherbee | 128/334 R |
| 963,899 | 7/1910 | Kistler | 128/334 R |
| 2,692,599 | 10/1954 | Creelman | 128/303 R |
| 2,845,925 | 8/1958 | Jayle | 128/334 R |
| 4,185,636 | 1/1980 | Gabbay et al. | 128/334 R |

FOREIGN PATENT DOCUMENTS

| 388739 | 10/1973 | U.S.S.R. | 128/334 R |

OTHER PUBLICATIONS

Gabbay–Frater Suture Guide Instructions for Professional Use only.
Annals of Thoracic Surgery, pp. 209–210, Jul.–Dec. 1981.

*Primary Examiner*—C. Fred Rosenbaum
*Assistant Examiner*—Gene B. Kartchner
*Attorney, Agent, or Firm*—Wells, St. John & Roberts

[57] ABSTRACT

A suture guide holder is described for releasably securing the "Gabbay-Frater" type suture guides in place adjacent a surgical incision held open by a retractor. The holder includes a rigid frame with a central opening for access to the incision area. The frame is adapted to rest directly on the arms of the retractor. It may also be secured to the surgical drapes at the incision site by spring clips extending downwardly from a bottom side of the frame. Upwardly protruding studs receive towel clip holes of the suture guides, securing the guides in position on the frame adjacent the incision.

16 Claims, 6 Drawing Figures

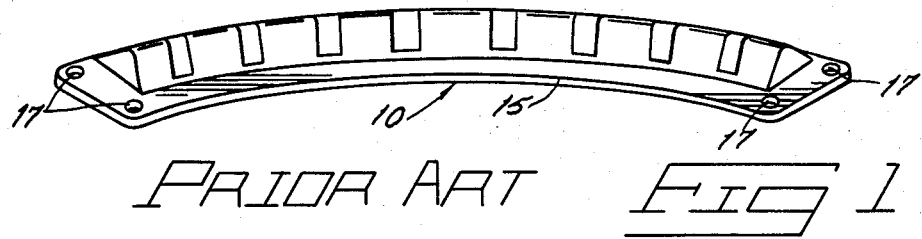
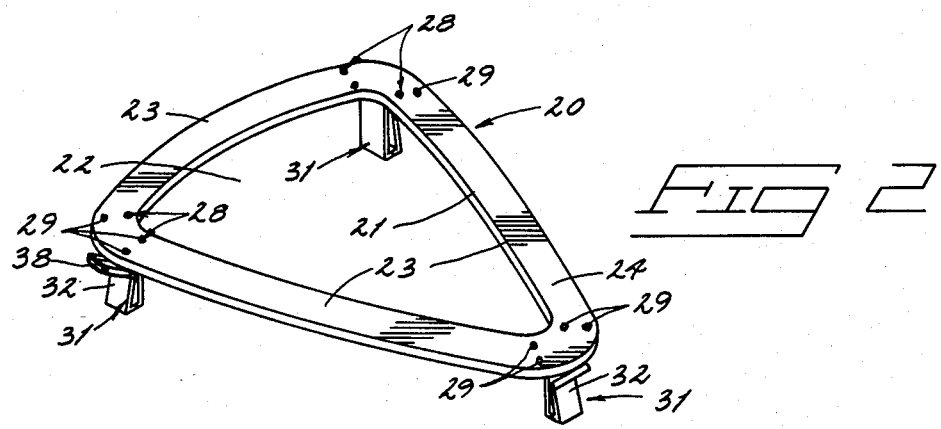
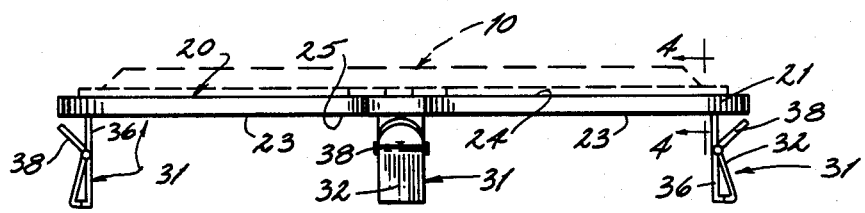
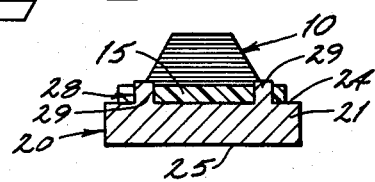

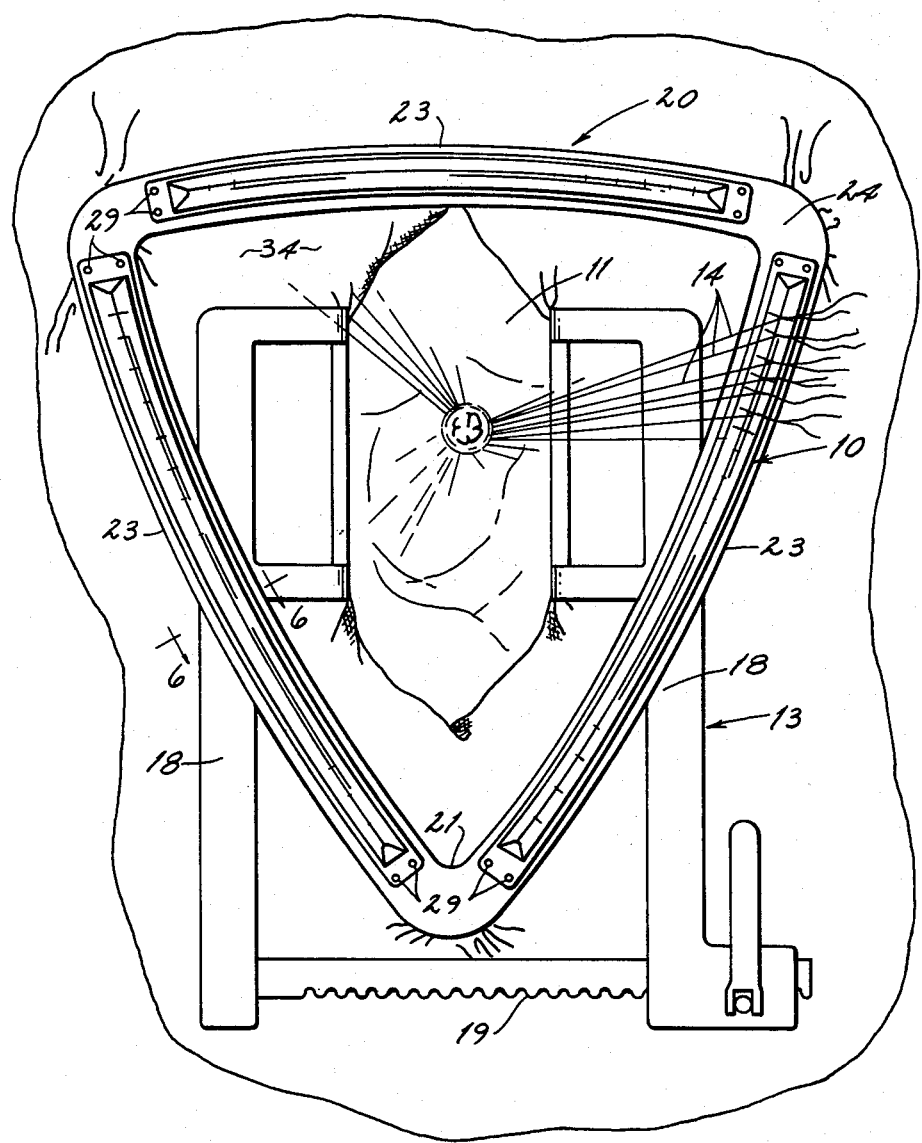
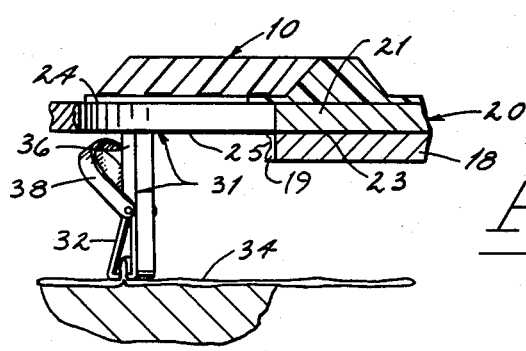
FIG 5
FIG 6

SUTURE GUIDE HOLDER

FIELD OF THE INVENTION

The present invention relates to securing surgical suture holders in position relative to an incision site.

BACKGROUND OF THE INVENTION

The "Gabby-Frater" suture guide (U.S. Pat. No. 4,185,636) has reduced the likelihood of confusion and disorder previously encountered in surgical procedures involving use of multiple interrupted sutures. This problem has been notably evident in several cardiac operations. For example, heart valve replacement, some anastomosis procedures and tetralogy repair require the use of multiple sutures.

Some procedures, such as mitral valve replacement, require the use of several suture holders. The holders are typically positioned around the incision site and secured to the surgical drapes by towel clips. The suture guides are formed of lightweight material and may be moved easily either intentionally or accidentally. A shift of the drape or "towel" material to which the guides are attached by clips will cause a corresponding motion of the suture guides. Frequently, such movements are no more than slight distractions and can be easily corrected by moving the holders back into position. There remains, however, the possibility that the holders will be displaced enough to seriously delay the procedure.

Another difficulty is noted especially in thoracic surgery wherein a chest retractor must be used to hold the incision open. The retractor arms are of necessity situated directly adjacent the sides of the incision and will not allow close positioning of the suture guides. Furthermore, the frame of the retractor projects above the incision area and obstructs efficient use of the guides.

The slight movement of a suture guide or the inconvenience of a retractor appear to be minor inconveniences. However, such "inconveniences" expend precious time during often critical surgery. It is very desirable to eliminate unnecessary use of time especially during the stages of an operation where the suture guide holders are used.

BRIEF DESCRIPTION OF THE DRAWINGS

A preferred form of the present invention is illustrated in the accompanying drawings in which:

FIG. 1 is a pictorial view of a prior art "Gabbay-Frater" suture guide;

FIG. 2 is a pictorial view of the present holder;

FIG. 3 is a side elevation of the holder;

FIG. 4 is an enlarged sectional view taken along line 4—4 in FIG. 3;

FIG. 5 is a pictorial view showing the present holder in position and resting on a chest retractor; and FIG. 6 is a detail view of a portion of the present holder.

DETAILED DESCRIPTION OF A PREFERRED EMBODIMENT

In compliance with the constitutional purpose of the Patent Laws "to promote the progress of science and useful arts" (Article 1, Section 8), applicant submits the following disclosure of the invention.

The present invention is intended for use to secure suture guides 10 in position adjacent to a surgical incision site 11. The suture guide shown in FIG. 1 is known as the "Gabby-Frater" guide and is disclosed in U.S. Pat. No. 4,185,636. Descriptive portions of that patent relating to the configuration and use of the disclosed suture guide holder are hereby incorporated by reference into this application.

FIGS. 1 and 5 illustrate the "Gabby-Frater" suture guide 10 alone and in position on the present holder 20 to secure sutures 14 (FIG. 5) in a prescribed order. Previously, as is disclosed in the above-referenced patent, the suture guides 10 were held in place adjacent the surgical side 11 by means of towel clips secured through appropriate towel clip holes 17 formed through a relatively flat base 15 of the guides.

It is noted that the suture guide 10 illustrated in the accompanying drawings is a commercial version somewhat different in appearance from the guide illustrated by the above-referenced patent. However, function and elements thereof remain essentially the same.

FIG. 5 illustrates the surgical incision site 11 held open by means of a rib retractor 13. Such retractors 13 typically include elongated arms 18 interconnected by an adjustable base member 19. In use, the arms and base member form a "U" configuration with the base member situated toward the abdomen from the incision site. The arms are adjustable over the length of the base and may be forced apart to spread the sternum and adjacent tissues for access to the underlying tissues.

The present holder is generally indicated at 20 in the drawings. The holder, basically, is used to receive and secure one or more of the suture guides 10 adjacent the surgical incision site 11.

The holder 20 includes a rigid frame 21 that is shown in the drawings as being somewhat triangular. The sides of the triangular configuration are arcuate to complement the typically arcuate configuration of suture guides 10.

FIGS. 2 through 4 show the substantially triangular configuration of the holder, including three arcuate sides 23. The sides are joined end-to-end to form an isosceles triangle with a central access opening 22. The size of the access opening 22 may vary with overall frame size, but is sufficient to allow free access to the incision site 11 when the frame is in place and surrounding the incision cavity. It is noted that the triangular shape is dependent only on the shape of the guides 10 and can therefore vary in overall shape, so long as the access opening remains an appropriate size.

The frame preferably includes a flat top surface 24 and a parallel flat bottom surface 25. The flat top surface 24 receives base flanges 15 (FIG. 4) of the suture guides 10. The flat bottom 25 is provided to rest against the arms 18 of the retractor 13 (FIGS. 3 and 6).

A mounting means 28 is provided on the annular frame for receiving and releasably securing the suture guides in place. The mounting means may comprise studs 29 extending upwardly from the flat top surface 24. The studs 29 are positioned to be received through towel clip holes 17 of the suture guides 10. The suture guides will snap over the studs 29 and the base flanges 15 thereof will rest flush against the flat frame top surface 24. There are at least two studs 29 provided for each suture guide 10 in order to hold the guide secure in position on the holder 20. The studs 29 are substantially cylindrical to allow removal of the suture guides 10 and restore the holder 20 for reuse.

A support means is generally shown at 31 on the frame member 21 for securing the frame member in a selected position relative to the incision site 11. The support means 31 may include the flat frame bottom 25 when the holder is rested on the arms 18 of a retractor 13. The flat bottom surface 25 will rest flush against the upper surfaces of the retractor arms 18. This positions the suture holder mounting means 28 on the top side of the frame member elevationally above the rib retractor 13. The retractor arms 18 therefore will not obstruct the suture length leading from the guides 10 to the operative area within the incision.

The support means 31 may also include a number of clips 32 operatively connected to the frame for attachment to the surgical drapes or towels 34 (FIGS. 4, 5) surrounding the incision site.

The clips 32 may be situated on upright legs 36 depending from the bottom frame side 25. The legs 36 may include clip jaw configurations at their lower ends to cooperate with spring biased clip jaw members 38. The jaw members 38 may be manually pivoted to open positions relative to the fixed legs and subsequently released to grip a fold of the surgical drape material 34 (FIG. 5). The legs 36 therefore will rest against the patient while the clip jaws grip the drapes 34, further assuring secure positioning of the holder 20, (FIG. 6).

The present holder 20 may be used in different surgical procedures wherein multiple interrupted sutures are required, especially in the vicinity of the chest where the rib retractor 13 must also be used to enable access to the operative area.

The suture guides 10 may be placed on the frame 21 prior to surgery. The entire assembly may then be quickly and easily positioned during the actual surgery at the time the suture guides are needed. The frame is then simply placed on the arms 18 of the rib retractor and the clips 32 attached to the adjacent surgical drapes below. The suture guides 10 can then be used at any time required. Removal of the present holder 10 is accomplished simply by reversing the above procedure.

Distinct advantages of the present holder have become evident through experimental use. It has been found that the holder more than adequately accomplishes its objective of securing the suture guides 10 firmly in position and within easy and fast access from the operative area. The combined support from the frame resting against the rib retractor arms, the legs 36, and the clips 32 assure a steady position for the suture guides during use.

In compliance with the statute, the invention has been described in language more or less specific as to structural features. It is to be understood, however, that the invention is not limited to the specific features shown, since the means and construction herein disclosed comprise a preferred form of putting the invention into effect. The invention is, therefore, claimed in any of its forms or modifications within the proper scope of the appended claims, appropriately interpreted in accordance with the doctrine of equivalents.

I claim:

1. A holder for elongated suture guides having towel clip mounting holes for releasably securing individual suture securing guides about a surgical incision site on a patient comprising:
   a rigid frame member made up of fixed rigid side sections having upper and lower surfaces and defining a central opening of a constant fixed configuration the approximate size of the surgical incision site extending between the upper and lower surfaces;
   mounting means on the upper surface of the frame member for receiving and releasably securing a number of suture securing guides to surround the incision site;
   support means on the frame member for securing the frame member to the patient in a selected position relative to the surgical incision site with the rigid frame member spaced clear of the incision and resting against the patient;
   upwardly projecting studs on the upper surface of the rigid frame adapted to be releasably received through the towel clip mounting holes; and
   wherein the studs are spaced about the frame in positions adapted to mount three suture guides in a triangular end-to-end relationship around the frame.

2. The holder of claim 1 for suture guides having towel clip mounting holes wherein the mounting means is comprised of:
   upwardly projecting studs on the upper surface of the annular frame member adapted to be releasably received through the towel clip mounting holes.

3. The holder of claim 1 wherein the frame is substantially triangular having three joined side sections and wherein the mounting means is adapted to releasably secure the suture guide on each of the three joined side sections.

4. The holder of claim 1 wherein the support means is comprised of: clips on the frame operable to secure the frame to surgical drapes about the surgical incision site.

5. The holder of claim 4 wherein the clips are spring clips with spring biased jaws operatively mounted to the lower surface of the frame.

6. The holder of claim 4 for use in surgery in conjunction with a rib retractor having a substantially flat upper surface;
   wherein the frame lower surface is flat to be received by the flat upper surface of the rib retractor.

7. The holder of claim 6 wherein the support means includes legs extending downwardly from the lower frame surface.

8. The holder of claim 7 wherein the support means further includes clips on the legs for attachment to surgical drapes covering the area adjacent the surgical incision site.

9. The holder of claim 8 for suture guides having towel clip mounting holes wherein the mounting means is comprised of:
   upwardly projecting studs on the upper surface of the annular frame member adapted to be releasably received through the towel clip mounting holes.

10. A holder for securing elongated suture guides having towel clip mounting holes about a surgical incision site comprising:
    a rigid frame member having upper and lower surfaces and a central opening of the approximate size of the surgical incision site extending between the upper and lower surfaces;
    support means on the frame member for securing the frame member in a selected position relative to the surgical incision site;
    mounting means on the upper surface of the frame member for receiving and releasably securing a suture guide; and
    wherein the mounting means is comprised of:

upwardly projecting studs on the upper surface of the rigid frame adapted to be releasably received through the towel clip mounting holes;

wherein the studs are spaced about the frame and in positions adapted to mount three suture guides in a triangular end-to-end relationship around the frame.

11. The holder of claim 10 wherein the frame is substantially triangular having three joined side sections and wherein the mounting means is adapted to releasably secure the suture guide on each of the three joined side sections.

12. The holder of claim 10 wherein the support means is comprised of:

clips on the frame operable to secure the frame to surgical drapes about the surgical incision site.

13. The holder of claim 12 wherein the clips are spring clips with spring biased jaws operatively mounted to the lower surface of the frame.

14. The holder of claim 12 for use in surgery in conjunction with a rib retractor having a substantially flat upper surface;

wherein the frame lower surface is flat to be received by the flat upper surface of the rib retractor.

15. The holder of claim 14 wherein the support means includes legs extending downwardly from the lower frame surface.

16. The holder of claim 15 wherein the support means further includes clips on the legs for attachment to the surgical drapes covering the area adjacent the surgical incision site.

* * * * *